United States Patent

Mars

(10) Patent No.: US 10,023,830 B2
(45) Date of Patent: Jul. 17, 2018

(54) SYSTEMS AND METHODS FOR THE CONTINUOUS OPTIMIZATION OF A MICROORGANISM CULTURE PROFILE

(71) Applicant: HELIAE DEVELOPMENT LLC, Gilbert, AZ (US)

(72) Inventor: Frank Mars, McLean, VA (US)

(73) Assignee: Heliae Development LLC, Gilbert, AZ (US)

( * ) Notice: Subject to any disclaimer, the term of this patent is extended or adjusted under 35 U.S.C. 154(b) by 99 days.

(21) Appl. No.: 14/802,058

(22) Filed: Jul. 17, 2015

(65) Prior Publication Data

US 2015/0322392 A1    Nov. 12, 2015

Related U.S. Application Data

(63) Continuation of application No. PCT/US2014/016512, filed on Feb. 14, 2014.
(Continued)

(51) Int. Cl.
*C12M 1/00* (2006.01)
*C12M 1/12* (2006.01)
(Continued)

(52) U.S. Cl.
CPC ......... *C12M 21/02* (2013.01); *C12M 23/06* (2013.01); *C12M 23/22* (2013.01); *C12M 23/58* (2013.01);
(Continued)

(58) Field of Classification Search
CPC ................ C12M 31/10; C12M 21/02
(Continued)

(56) References Cited

U.S. PATENT DOCUMENTS 6,416,993 B1 * 7/2002 Wexler ............... C02F 3/32
    210/601
6,602,703 B2    8/2003 Dutil
(Continued)

FOREIGN PATENT DOCUMENTS

CN    202022929    11/2011
JP    2012029578    2/2012
(Continued)

OTHER PUBLICATIONS

Giannelli et al., Hydrogen production with the microalga *Chlamydomonas reinhardtii* grown in a compact tubular photobioreactor immersed in a scattering light nanoparticle suspension, 2012, International Journal of Hydrogen Energy, 37, pp. 16951-16961.*
(Continued)

*Primary Examiner* — Kevin Joyner
*Assistant Examiner* — Holly M Mull
(74) *Attorney, Agent, or Firm* — Heliae Development LLC; Veronica-Adele R. Cao; Justin Kniep (57) ABSTRACT

Systems and methods are disclosed for continuously optimizing the profile of an aqueous culture comprising microorganisms. The systems and methods comprise a controlled environment comprising a housing enclosing a lighting device and controlled temperature environment, and sensor modules for measuring culture and environment parameters. The sensor modules may be in communication with an automated computer control system to continuously optimize the microorganism culture profile.

17 Claims, 5 Drawing Sheets

Related U.S. Application Data (60) Provisional application No. 61/768,937, filed on Feb. 25, 2013.

(51) Int. Cl.
  *C12M 1/18*  (2006.01)
  *C12M 1/02*  (2006.01)
  *C12M 1/34*  (2006.01)
  *C12M 1/36*  (2006.01)

(52) U.S. Cl.
  CPC ............ *C12M 29/18* (2013.01); *C12M 31/02* (2013.01); *C12M 31/10* (2013.01); *C12M 41/18* (2013.01); *C12M 41/26* (2013.01); *C12M 41/48* (2013.01)

(58) Field of Classification Search
  USPC ...................................... 435/292.1
  See application file for complete search history.

(56) References Cited

U.S. PATENT DOCUMENTS

| | | | |
|---|---|---|---|
| 7,851,211 B2 | 12/2010 | Lu | |
| 8,642,326 B1 * | 2/2014 | Schaefer | A01G 33/00 435/257.1 |
| 2009/0011492 A1 * | 1/2009 | Berzin | B01D 53/84 435/257.1 |
| 2010/0151558 A1 * | 6/2010 | Alianell | C12M 21/02 435/257.3 |
| 2010/0261260 A1 * | 10/2010 | Morgan | B01D 53/007 435/257.3 |
| 2011/0020913 A1 * | 1/2011 | Rispoli | C12M 21/02 435/257.1 |
| 2012/0021505 A1 * | 1/2012 | Kim | C12M 21/02 435/292.1 |
| 2012/0122199 A1 * | 5/2012 | Kabakian | C12M 21/02 435/292.1 |
| 2012/0156762 A1 * | 6/2012 | Csanyi | C12M 21/02 435/257.1 |
| 2012/0171733 A1 * | 7/2012 | Im | A01G 33/00 435/101 |
| 2012/0252105 A1 * | 10/2012 | Ahrens | C12M 21/02 435/257.3 |

FOREIGN PATENT DOCUMENTS

| | | | | |
|---|---|---|---|---|
| WO | 2008097845 | | 8/2008 | |
| WO | 2009149519 | | 12/2009 | |
| WO | WO 2010115655 A1 * | 10/2010 | ............ | C12M 21/02 |
| WO | 2012024406 | | 2/2012 | |

OTHER PUBLICATIONS

Facciolo. A study on axially rotating pipe and swirling jet flows. Feb. 2006 Technical reports from Royal Institute of Technology, Department of Mechanics, S-100 44 Stockholm, Sweden. Accessed online Oct. 15, 2012 at: hllp://www.diva-portal.org/smach/get/diva2:9755/FULLTEXT01.pdf.

Chapter 3 Rotational Flows: Circulation and Turbulence. Accessed online Oct. 15, 2012 at: http://maxwell.ucdavis.edu/~cole/phy9b/notes/fluids_ch3.pdf.

Poroseve, et al. Computation of turbulence Research, Annual Research Briefs 2000, pp. 279-290.

Reich, et al. Fluid flow and heat transfer in an axially rotating pipe—II. Effect of rotation on laminar pipe flow. Int. J. Heat Mass Transfer, vol. 32, No. 3, pp. 563-574, 1989.

* cited by examiner

SYSTEMS AND METHODS FOR THE CONTINUOUS OPTIMIZATION OF A MICROORGANISM CULTURE PROFILE

CROSS REFERENCE TO RELATED APPLICATIONS

This application claims the benefit of PCT Application No. PCT/US2014/016512, filed Feb. 14, 2014, entitled Systems and Methods for the Continuous Optimization of a Microorganism Culture Profile, U.S. Provisional Application No. 61/768,937, filed Feb. 25, 2013, entitled Systems and Methods for the Continuous Optimization of a Microorganism Culture Profile, the entire contents of which are hereby incorporated by reference.

BACKGROUND

A culture of microorganisms, such as microalgae and cyanobacteria, may change composition (e.g., proteins, lipids, pigments) and stages (e.g., growth, lipid accumulation) due to a plurality of culture parameters providing input to the cell. Examples of parameters of a microorganism culture which may change during the culturing period comprise, light exposure, pH, gas levels, nutrient levels, and temperature, which may affect the composition on a cellular level and culture level, such as density of the microorganisms, health of the microorganisms, life stage of the microorganisms (e.g., growth, lipid accumulation), culture composition (i.e. different types of microorganisms, organic materials, inorganic materials), and contamination level (e.g., predators, competing species, toxins, excreted products, bacteria, fungi). If one or more of the culture parameters fall below or rise above an optimal range, the microorganisms may perish, experience a decline in growth, or limit production of target products such as lipids, pigments, and proteins. In a commercial production setting, even small effects of the culture parameters outside of an optimal profile may result in losses due to decreased yield and increased costs.

For example, photosynthetic microorganisms use the energy provided by light in conjunction with carbon dioxide to produce chemical energy that is usable by the microorganisms for various cellular activities. Light of different wavelengths will affect the photosynthetic microorganism activities in different manners, including inhibiting activities in some instances. For example, light in the red wavelength spectrum (about 620-750 nm) may promote growth and cell division, while large amounts of light in the blue wavelength spectrum (about 450-495 nm) may lead to a loss in electron transfer in photosystem II of the cell and require repairs to photosystem II. Some wavelengths of light may even kill microorganisms if applied at the proper intensity and for the proper duration. In typical outdoor conditions where photosynthetic microorganisms receive solar energy, the photosynthetic microorganism is exposed to a wide variety of light wavelengths, some of which can cause photoinhibition and heating of the culture. Using the example of how light may affect photosynthetic microorganisms, the application of light may be used to control some of the conditions of a culture. However, the complex relationships between culture parameters can cause multiple parameters to change when a single parameter, such as light intensity, is applied to a culture.

For instance, a change in light intensity may increase the growth activity driven by photosynthesis may also affect the temperature and pH due to increased carbon dioxide consumption which may produce a negative effect on the microorganisms. With the potential for culture parameters to change quickly, and a culture may need to be monitored closely enough for corrective action to be taken before the culture is beyond a point of recovery. The ability to teach a system to learn and adapt continuously can make the difference between a culture of microorganisms perishing (resulting in a complete loss), and a productive harvest of the microorganisms. Conventional bioreactor systems are focused on a single task, which is typically growth, and may be designed specifically for parameters preferred by a single species or type of microorganism. The lack of flexibility of conventional bioreactors to continuously monitor a culture for adaptation, or to adjust to different parameters preferred by a different species or type of microorganisms leads to inefficient production.

Therefore, there is a need in the art for systems and methods to continuously monitor and control the parameters of a microorganism culture to maintain a culture profile optimized for a target characteristic, such as health, longevity, or production of a particular product.

SUMMARY

Systems and methods are disclosed for continuously optimizing the profile of an aqueous culture comprising microorganisms. Continuous monitoring and a controlled environment are used to adjust parameters to within a desired range to form a profile for a desired purpose.

In one embodiment, a controlled environment apparatus may comprise: a housing comprising an interior volume; at least one lighting device comprising an artificial light source disposed within the interior volume of the housing; at least one culture pipe configured to hold an aqueous culture medium comprising microorganisms, wherein the at least one culture pipe comprises a transparent material and is disposed at least partially within the interior volume of the housing; and a temperature control device configured to control the temperature of the interior volume within the housing.

In some embodiments the artificial light source may comprise at least one selected from the group consisting of light emitting diodes (LEDs), micro-LEDs, and light bulbs. In some embodiments, the artificial light source may emit light in at least one limited wavelength range selected from the group consisting of: violet (about 380-450 nm), blue (about 450-495 nm), green (about 495-570 nm), yellow (about 570-590 nm), orange (about 590-620 nm), red (about 620-750 nm), far red (about 700-800 nm), infrared (IR) (about 1,000-20,000 nm) and ultraviolet (UV) (about 10-400 nm). In some embodiments, the at least one lighting device may comprise at least one selected form the group consisting of: a continuous light source along the length of the housing and discretely spaced light sources within the housing. In some embodiments, the at least one lighting device may be disposed in at least one location selected from the group consisting of: on an exterior surface of the at least one culture pipe, on an interior surface of the housing, and within at least one lighting pipe.

In some embodiments, the temperature control device may comprise at least one selected from the group consisting of: an HVAC unit, a heat exchanger, heating coils, cooling coils, and a fan. In some embodiments, the apparatus may further comprise at least one bracket disposed within the interior volume of the housing and configured to support at least one selected form the group consisting of the at least one culture pipe and the at least one lighting device. In some embodiments, the at least one lighting device is disposed on the at least one bracket.

In another embodiment, a method for continuously optimizing the profile of a microorganism culture may comprise: growing a culture of microorganisms in an aqueous medium in a culturing vessel exposed to an ambient environment; removing at least a portion of the aqueous culture form the culturing vessel and transferring the removed aqueous culture to at least one culture pipe; measuring at least one parameter of the removed aqueous culture from the culturing vessel and transferring the removed aqueous culture to at least one culture pipe; measuring at least one parameter of the removed aqueous culture and ambient environment with at least one sensor before the aqueous culture enters a housing; flowing the removed aqueous culture through the at least one culture pipe from a first end of the at least one culture pipe to a second end of the at least one culture pipe, wherein the at least one culture pipe is at least partially disposed within an interior volume of the housing; applying light to the removed aqueous culture flowing through a transparent length of the at least one culture pipe between the first end and the second end disposed within the interior volume of the housing with at least one lighting device disposed within an interior volume of the housing; and controlling the temperature of the interior volume within the housing.

In some embodiments, the method may further comprise measuring at least one parameter of the removed aqueous culture with at least one sensor at a location after the removed aqueous culture exists the housing. In some embodiments, the method may further comprise returning the removed aqueous culture to the culturing vessel. In some embodiments, the method may further comprise processing the removed culture in a culture processing device in at least on from the group consisting of: a mixing process, nutrient addition, gas exchange, pH adjustment, contamination control, removal of biomass, and water removal. In some embodiments, the steps of measuring the at least one parameter of the removed aqueous culture may further comprise fluorescing the removed culture to detect the composition of the culture.

In some embodiments, the step of applying light may further comprise applying light of at least one limited wavelength range selected from the group consisting of: violet (about 380-450 nm), blue (about 450-495 nm), green (about 495-570 nm), yellow (about 570-590 nm), orange (about 590-620 nm), red (about 620-750 nm), far red (about 700-800 nm), infrared (IR) (about 1,000-20,000 nm) and ultraviolet (UV) (about 10-400 nm). In some embodiments, the step of controlling the temperature of the interior volume within the housing may comprise at least one selected from the group consisting of: circulating a cooling fluid in the interior volume, circulating a heating fluid in the interior volume, circulating air in the interior volume, and operating a heat exchanger. In some embodiments, the at least one parameter measured by the at least one sensor may comprise at least one selected from the group consisting of: culture pH, culture nutrient levels, culture gas levels, culture composition, culture health, contamination levels, culture temperature, flow rate, culture density, ambient environment temperature, and ambient environment light.

In some embodiments, the method may further comprise adjusting with an automated computer controller receiving data comprising the at least one parameter measured by the at least one sensor at least one from the group consisting of: flow rate, temperature of the interior volume of the housing, light application within the interior volume of the housing, culture mixing, nutrient addition to the culture, gas exchange with the culture, contamination control, removal of biomass, and removal of water.

In another embodiment, a system for continuously optimizing the profile of a culture of microorganisms may comprise: a culturing vessel configured to grow microorganisms in an aqueous medium; a housing comprising an interior volume; at least one artificial lighting device disposed within the interior volume of the housing; at least one culture pipe with a first end and a second end in fluid communication with the culturing vessel, configured to hold an aqueous culture medium comprising microorganisms, and wherein the at least one culture pipe comprises a transparent portion disposed at least partially within the interior volume of the housing; a first sensor module disposed in a first location to measure at least one parameter at the first end of the at least one culture pipe; and a temperature control device for controlling the temperature of the interior volume within the housing.

In some embodiments, the system may further comprise a second sensor module disposed in a second location to measure at least one parameter at the second end of the at least one culture pipe. In some embodiments, the system may further comprise at least one culture processing device in fluid communication with the at least one culture pipe. In some embodiments, the system may further comprise a pump to circulate the aqueous medium through the system. In some embodiments, the culture processing device may comprise at least one selected from the group consisting of: a mixing device, pH adjustment device, a contamination control device, a gas exchange device, a nutrient addition device, a biomass removal device, and a water removal device.

In some embodiments, at least one of the first sensor module and the second sensor module may comprise at least one sensor selected from the group consisting of: temperature, carbon dioxide, ozone, redox potential, dissolved oxygen, light (watts/meter$^2$), light ($\mu$mols/meter$^2$ day), light wavelength (nm), relative humidity, air speed, pH, chlorophyll A, phycobilins, phycocyanins, turbidity, color, density, salt content/concentration, optical density, electrical conductivity sensors, and fluorescence. In some embodiments, the system may further comprise an automated computer controller, wherein the automated computed controller is configured to continuously receive data from the first and second sensor modules and adjust at least one from the group consisting of: a flow rate of the removed culture, temperature of the interior space of the housing, light application within the interior space, culture mixing, nutrient addition of the culture, gas exchange with the culture, contamination control, removal of biomass, and removal of water.

In another embodiment, an apparatus may comprise: means for enclosing an interior volume; means for flowing an aqueous culture of microorganisms through the interior volume; and means for supplying light to the aqueous culture of microorganisms in the interior volume to maintain a desired profile in the culture of microorganisms. In some embodiments, the apparatus may further comprise means for controlling the temperature of the interior volume to maintain a desired profile in the culture of microorganisms.

In another embodiment, a system may comprise: means for culturing microorganisms in an aqueous culture medium; means for measuring at least one parameter of the culture of microorganisms; and means for utilizing the at least one measured parameter to control temperature and light of a closed environment to maintain a desired profile of the culture of microorganisms.

DETAILED DESCRIPTION

The term "microorganism" refers to microscopic organisms such as microalgae and cyanobacteria. Microalgae include microscopic multi-cellular plants (e.g. duckweed), photosynthetic microorganisms, heterotrophic microorganisms, diatoms, dinoflagelattes, and unicellular algae.

The terms "microbiological culture", "microbial culture", or "microorganism culture" refer to a method or system for multiplying microorganisms through reproduction in a predetermined culture medium, including under controlled laboratory conditions. Microbiological cultures, microbial cultures, and microorganism cultures are used to multiply the organism, to determine the type of organism, or the abundance of the organism in the sample being tested. In liquid culture medium, the term microbiological, microbial, or microorganism culture generally refers to the entire liquid medium and the microorganisms in the liquid medium regardless of the vessel in which the culture resides. A liquid medium is often referred to as "media", "culture medium", or "culture media". The act of culturing is generally referred to as "culturing microorganisms" when emphasis is on plural microorganisms. The act of culturing is generally referred to as "culturing a microorganism" when importance is placed on a species or genus of microorganism. Microorganism culture is used synonymously with culture of microorganisms.

The terms "phototrophic", "phototrophy", "photoautotrophy", "photoautotrophic", and "autotroph" refer to culture conditions in which light and inorganic carbon (e.g., carbon dioxide, carbonate, bi-carbonate) may be applied to a culture of microorganisms. Microorganisms capable of growing in phototrophic conditions may use light as an energy source and inorganic carbon (e.g., carbon dioxide) as a carbon source. A microorganism in phototrophic conditions may produce oxygen.

The terms "mixotrophic" and "mixotrophy" refer to culture conditions in which light, organic carbon, and inorganic carbon (e.g., carbon dioxide, carbonate, bi-carbonate) may be applied to a culture of microorganisms. Microorganisms capable of growing in mixotrophic conditions have the metabolic profile of both phototrophic and heterotrophic microorganisms, and may use both light and organic carbon as energy sources, as well as both inorganic carbon and organic carbon as carbon sources. A mixotrophic microorganism may be using light, inorganic carbon, and organic carbon through the phototrophic and heterotrophic metabolisms simultaneously or may switch between the utilization of each metabolism. A microorganism in mixotrophic culture conditions may be a net oxygen or carbon dioxide producer depending on the energy source and carbon source utilized by the microorganism. Microorganisms capable of mixotrophic growth comprise microorganisms with the natural metabolism and ability to grow in mixotrophic conditions, as well as microorganisms which obtain the metabolism and ability through modification of cells by way of methods such as mutagenesis or genetic engineering.

The terms "heterotrophic" and "heterotrophy" refer to culture conditions in which organic carbon may be applied to a culture of microorganisms in the absence of light. Microorganisms capable of growing in heterotrophic conditions may use organic carbon as both an energy source and as a carbon source. A microorganism in heterotrophic conditions may produce carbon dioxide.

The organic carbon sources suitable for growing a microorganism mixotrophically may comprise: acetate, acetic acid, ammonium linoleate, arabinose, arginine, aspartic acid, butyric acid, cellulose, citric acid, ethanol, fructose, fatty acids, galactose, glucose, glycerol, glycine, lactic acid, lactose, maleic acid, maltose, mannose, methanol, molasses, peptone, plant based hydrolyzate, proline, propionic acid, ribose, sacchrose, partial or complete hydrolysates of starch, sucrose, tartaric, TCA-cycle organic acids, thin stillage, urea, industrial waste solutions, yeast extract, and combinations thereof. The organic carbon source may comprise any single source, combination of sources, and dilutions of single sources or combinations of sources.

Microorganisms, such as microalgae and cyanobacteria, may be grown in a culture comprising a freshwater or marine (i.e., saltwater) aqueous medium in a natural environment such as, but not limited to, ponds or lakes. Microorganisms may also be grown in an artificial environment such as, but not limited to, vessels, photobioreactors, raceway ponds, tubular bioreactors, bags, tanks, and troughs. Non-transparent vessels, such as opaque tanks, and other vessels of varying levels of transparency may be used to grow heterotrophic and mixotrophic microorganisms in the absence of light or in low light conditions where nutrients, gas transfer, temperature, and other parameters are controlled. Photobioreactors may be used to grow phototrophic and mixotrophic microorganisms in a both open and closed artificial environment where light, nutrients, gas transfer, temperature, and other parameters are controlled in bags, tubes, pipes, flat panel vessels, tanks, troughs, raceway ponds, or any other suitable culturing vessel allowing exposure to as least some amount of light. In both a natural environment and artificial environment, all cultures of microorganisms have a profile of parameters such as, but not limited to, light exposure, pH, gas levels, nutrient levels, and temperature. The ability to maintain the culture in an optimal profile of parameters requires the culturing system to continuously monitor and adjust as the environment and metabolic activity of the microorganisms changes the parameter profile.

In particular, cultures of phototrophic and mixotrophic microorganisms may be exposed to the light and temperature of the ambient environment when cultured in open outdoor systems. Additionally, in both a natural environment and an artificial environment phototrophic and mixotrophic organisms may be exposed to solar energy and/or artificial light, such as but not limited to, incandescent lights, fluorescent lights, light emitting diodes (LED), and micro-LEDs. Artificial lights may be selected or tuned to provide light of a particular wavelength spectrum or combination of spectrums such as, but not limited to, violet (about 380-450 nm), blue (about 450-495 nm), green (about 495-570 nm), yellow (about 570-590 nm), orange (about 590-620 nm), red (about 620-750 nm), and far red (about 700-800 nm). Artificial lights may also provide light outside the visible spectrum such as, but not limited to, infrared (IR) (about 1,000-20,000 nm) and ultraviolet (UV) (about 10-400 nm).

For all microorganism cultures, a system and method for continuously monitoring and controlling not only light but other parameters such as, but not limited to, temperature, nutrients, gases, to maintain the culture contamination, culture composition and microorganism density, and microorganism product profile in an optimal range. A system and method which continuously monitors and adapts to the culture conditions to maintain an optimal culture profile will increase the efficiency of culturing microorganisms and increases yield of the cultured microorganism or targeted products. The systems and methods described may be applicable to a wide variety of different microorganism species that have different preferred culture conditions and produce different products from various stresses (e.g., light, temperature, lack of nutrients) through the ability to continuously adapt and adjust to changing parameters.

System

A system for continuously optimizing the profile of a culture of microorganisms, may comprise: a culturing vessel configured to grow microorganisms in an aqueous medium; a housing comprising an interior volume; at least one artificial lighting device disposed within the interior volume of the housing; at least one culture pipe with a first end and second end in fluid communication with the culturing vessel and configured to hold an aqueous culture medium comprising microorganisms, wherein the at least one culture pipe may comprise a light transmissive or transparent portion disposed at least partially within the interior volume of the housing; a first sensor module disposed in a first location to measure at least one culture and/or ambient environmental parameter at the first end of the at least one culture pipe; a second sensor module disposed in a second location to measure at least one culture parameter at the second end of the at least one culture pipe; and a temperature control device for controlling the temperature of the interior volume of the housing. The system may further comprise at least one culture processing device in fluid communication with the at least one culture pipe and an automated computer controller (e.g., programmable logic controller (PLC)), wherein the automated computer controller continuously receives the culture parameters measured by the sensors and adjusts at least one from the group consisting of: a flow rate of the culture through the at least one culture pipe, temperature of the interior volume of the housing, light application within the interior volume of the housing, culture mixing, nutrient addition to the culture, gas exchange with the culture, contamination control, removal of biomass and removal of water. The system may further comprise a pump to circulate the aqueous medium through the system.

Culturing Vessel

The culturing vessel may comprise any natural or artificial vessel in which microorganisms are cultured in an aqueous culture medium such as, but not limited to: lakes, ponds, pools, raceway ponds, troughs, tanks, fermenters, photobioreactors, tubular reactors, flat panel reactors, and bag reactors. The culturing vessel may be in fluid communication with the other components of the system to allow a portion of aqueous culture to be diverted from the culturing vessel for processing through the system and then return to the culturing vessel on a continuous basis or intermittent basis.

Culture Processing Device

The at least one culture processing device may comprise devices capable of operations such as, but not limited to: mixing, addition of nutrients, pH adjustment, gas exchange, contamination control, biomass removal, and water removal. Non-limiting examples of devices which can perform culture processing comprise, but are not limited to, foam fractionation devices, protein skimmers, UV sterilizers, centrifuges, devices applying an electric field to the culture, filters, membranes, liquid injectors, and gas injectors. The at least one culture processing device may be located within the system before or after the housing to perform culture processing before, after, or both before and after the aqueous culture enters the housing.

Housing

The housing may comprise a material that isolates the interior volume of the housing from light striking the exterior of the housing and aids in the optimization of the application of light, blocking of at least some light, and/or control of temperature for the culture of microorganisms passing through the housing on a continuous basis. In some embodiments, the housing material may be completely opaque and block substantially all light from passing through. In some embodiments, the housing material may not be completely opaque, and allow only light of a selected wavelength to pass through. In some embodiments, the shape of the housing may comprise a closed cylinder with a circular or elliptical shaped cross-section forming circular or elliptical end walls and a curved side wall. In some embodiments, the shape of the housing may comprise a closed box with a polygonal, square, or rectangular shaped cross-section forming rectangular or polygonal shaped end walls and side walls. In some embodiments, at least one side wall or end wall may have at least one aperture for the at least one lighting device and/or the at least one culture pipe to pass through. In further embodiments, the at least one aperture may be sized to minimize the clearance between the device or pipe passing through the opening or fitted with a flexible seal, in order to reduce the amount of light that enters the interior volume of the housing through the aperture and to aid in controlling the temperature within the housing.

The dimensions of the housing may be determined by aspects such as: the number of artificial lighting devices and culture pipes contained in the interior space of the housing, the length of the at least one artificial lighting device and culture pipe, the spatial arrangement of the at least one artificial lighting device and culture pipe, and the desired residence time for the exposure of the culture of microorganisms to the controlled environment comprising a desired wavelength of light, absence of light and/or desired temperature within the housing. In some embodiments, the at least one artificial lighting device and culture pipe extend between a pair of end walls of the housing, and run parallel to each other and the sidewalls of the housing. The thickness of the walls of the housing may be determined by features such as: the light transmissibility of the housing material and the desired thermal insulation properties of the housing material. In some embodiments, the interior of the housing may comprise a reflective material capable of reflecting the light provided by the at least one lighting device within the interior of the closed housing. In some embodiments, the housing materials may be any suitable opaque material such as, but not limited to, wood, metal, plastic, fiberglass, and vinyl. In some embodiments, the housing material may be transparent to some degree (0-100%) and include a film, coating, or composition that blocks all light or at least some light of a selected wavelength spectrum.

In some embodiments, the housing may also include at least one bracket spaced along the longitudinal axis of the housing. The at least one bracket may provide structural support for the at least one light device and culture pipe over the length of the housing, as well as maintaining spacing and parallel orientation between the pipes. The at least one bracket may comprise at least one aperture to allow each light device and culture pipe to pass through the at least one bracket. The surface area of the at least one bracket may also be minimized to allow for fluid communication of the controlled environment (e.g., temperature controlled fluids, gases, air, water) throughout the entire housing interior volume. The minimal surface area of the at least one bracket may be achieved through cut-outs and apertures. In some embodiments, the at least one bracket may be built into the housing or fastened to the housing at fixed locations. In some embodiments, the at least one bracket may be unattached to the housing to allow the at least one bracket to be repositioned within the housing. The at least one bracket may comprise any suitable rigid material such as, but not limited to, glass, wood, metal, plastic, and fiberglass. The at least one bracket may be completely opaque, or transparent to a desired degree (0-100%) to allow the transmission of all or at least selected wavelengths of light. In some embodiments, the housing may not include the at least one bracket, and may provide support for the at least one light device and culture pipe by apertures and/or cut outs in the end walls and/or side walls of the housing.

Lighting Device

The at least one lighting device may be any known artificial light source capable of installation in the interior volume of the housing. The at least one lighting device may emit light of a desired wavelength spectrum or spectrums within the interior volume of the housing. The at least one lighting device may be any artificial light source which emits light in one wavelength spectrum or a plurality of wavelength spectrums, such as, but not limited to violet (about 380-450 nm), blue (about 450-495 nm), green (about 495-570 nm), yellow (about 570-590 nm), orange (about 590-620 nm), red (about 620-750 nm), far red (about 700-800 nm), infrared (IR) (about 1,000-20,000 nm), and ultraviolet (UV) (about 10-400 nm). The at least one lighting device and wavelength spectrums may be selected based on aspects such as, but not limited to, the characteristics of the organisms of the culture, the composition of the culture, the desired effect on an organism, the end products desired from an organism, heat output, and energy usage. The at least one lighting device may receive power from an external power source, including electricity produced by photovoltaic panels.

In some embodiments, the at least one lighting device may comprise light emitting diodes (LEDs) or micro-LEDs. In some embodiments, the at least one lighting device may emit at least two different wavelength spectrums. In further embodiments, the at least one lighting device may comprise LEDs or micro-LEDs for emitting a plurality of selected wavelength spectrums such as, but not limited to, light of a first wavelength, a second wavelength, and a third wavelength spectrum. In one non-limiting embodiment of the invention, LEDs providing the first, second, and third wavelength spectrum may all emit light in combination simultaneously. In another non-limiting embodiment of the invention, the LEDs providing the first, second, and third wavelength spectrum may be independently controlled to provide light individually (e.g., only one spectrum at a time), in combination with another spectrum (e.g., combinations of two spectrums), or in a predetermined sequence of spectrums individually or spectrum combinations (e.g., alternating between two spectrums; alternating between more than two spectrums; combination of first and second spectrum, then combination of first and third spectrum, then combination of second and third spectrum). In some embodiments, the wavelength of light emitted may be manually selected. In some embodiments, the wavelength of light may be selected by an automated computer controller (e.g., programmable logic controller) in response to data received from sensor modules. In some embodiments, the artificial light source may be continuous along the length of the lighting device.

The duration of light application may also be selected to produce a desired outcome within the culture of microorganisms such as, but not limited to, maximizing culture biomass growth, enhancing the production of a targeted product (e.g., lipids, pigments, phytohormones, proteins), and controlling contamination within the culture by killing contamination organisms (e.g., bacteria, rotifers, fungi, undesired microorganism species). In some embodiments, the at least one lighting device may be turned off to provide a dark period for the culture of microorganisms while the aqueous culture flows through the housing of the apparatus. In some embodiments, the at least one lighting device may be on continuously for the continuous application of light. In some embodiments, the at least one lighting device alternates between an on and off position to provide light in an intermittent, pulsing, or flashing application. The intensity of the light application may also be varied for a desired outcome. In some embodiments, the light application may be at a constant intensity. In some embodiments, the light application may fluctuate to increase or decrease the intensity.

In one non-limiting exemplary embodiment, the at least one lighting device may comprise at least one lighting pipe. In some embodiments, the at least one lighting pipe may comprise a transparent pipe material and an artificial light source contained within the pipe. The transparent pipe material may be any suitable material which allows transmission of the desired wavelength, such as, but not limited to, glass or plastic. In some embodiments, the at least one lighting pipe may comprise a transparent pipe and a film or coating which selectively allows the transmission of light of desired wavelength spectrums. The thickness of the pipe material may comprise any thickness which sufficiently transmits light out of the pipe without significant degradation or refraction of the light. The length of the at least one lighting pipe may be determined by the desired amount of light to be emitted within the housing. The diameter of the at least one lighting pipe may be determined by the physical space needed to enclose the artificial light source.

In some embodiments, the at least one lighting pipe may be comprised of a pipe with a flexible substrate of LEDs wrapped on the exterior of the pipe, with the LEDs emitting light away from the pipe surface. In some embodiments, the at least one lighting pipe may be comprised of a transparent pipe material with a flexible substrate of LEDs on the interior surface of the pipe, with the LEDs emitting light through the pipe walls. In some embodiments, the at least one lighting pipe may be comprised of a transparent pipe with a panel or module of LEDs in the interior space of the pipe, with the LEDs emitting light through the pipe walls. In some embodiments, the at least one lighting pipe may comprise at least one light bulb such as, but not limited to, a fluorescent bulb. In some embodiments, the cross-section of the at least one lighting pipe may be circular, elliptical, square, rectangular, or polygonal. In some embodiments, the length of the at least one lighting pipe may extend beyond the length of the housing and through an opening in at least one end or side wall.

In an alternative embodiment, the light source of the at least one lighting device may be non-continuous. The light sources of the at least one lighting device may be disposed at discrete locations within the interior volume of the housing, spaced along the length of the at least one lighting device, and combinations thereof. In another alternative embodiment, artificial light sources may be disposed on the interior surface of the housing and/or at least one bracket in combination with or instead of a separate lighting device. The light sources disposed on the interior surface of the housing and/or at least one bracket may be on one surface, on multiple surfaces, continuous, or spaced at discrete locations.

In another alternative embodiment, at least one lighting device may be disposed directly on the outer surface of the at least one culture pipe in combination with or instead of a separate lighting device. The lights disposed on the outer surface of the at least one culture pipe may be disposed on the inner surface of a clamp like structure which fits around the exterior of the culture pipe, allowing light to shine into the at least one culture pipe. The lights may also comprise a flexible substrate of LEDs or micro LEDs which may be wrapped around the exterior of the at least one culture pipe and transmits light into the interior of the at least one culture pipe. The light sources disposed on the outer surface of the at least one culture pipe may be continuous or spaced at discrete locations.

In another alternative embodiment, the at least one lighting device may comprise a flat panel of lights disposed within interior space of the housing. The at least one culture pipe may be disposed adjacent to the flat panel to receive light emitted from the flat panel of lights. The lights may be disposed continuously or spaced at discrete locations on the flat panel. The flat panel may be disposed horizontally, vertically or at any angle. The flat panel of lights may be used in combination with or instead of a lighting pipe or other light source.

Temperature Control

The temperature of the interior volume of the housing may also be controlled. Temperature of a gas (e.g., air), liquid (e.g., water), or other fluid contained in, circulating within, or flowing through the interior volume may be controlled by any temperature control device known in the art such as, but not limited to an HVAC (heating, ventilating, and air conditioning) unit, heat exchangers, heating/cooling coils, and fans. In some embodiments, the heating and/or cooling systems controlling the temperature may comprise an evaporative cooling system, natural gas heating systems, natural gas cooling/refrigeration systems, or any other known heating/cooling system in the art. In some embodiments, the heating and/or cooling systems controlling the temperature may utilize geothermal heat and/or recovered waste heat from another industrial process co-located with the system for optimizing a microorganism culture profile.

In some embodiments, the interior volume of the housing may be heated to increase or maintain the temperature of the culture of microorganisms as the culture passes through the housing in the at least one culture pipe. In some embodiments, the volume within the housing may be cooled to decrease or maintain the temperature of the culture of microorganisms as the culture passes through the housing in the at least one culture pipe. In some embodiments, fans may circulate air or other gases within the interior volume of the housing. In some embodiments, the environment within the interior of the lighting pipe may be heated or cooled by a fluid, such as water or air, flowing through the lighting pipe.

In some embodiments, the fluid used in the interior of the lighting pipe may dissipate heat produced by the artificial light source.

Culture Pipe

The at least one culture pipe provides a conduit for flowing the aqueous culture medium comprising microorganisms through the system, including the segment of the system comprising the interior volume of the housing for controlled exposure to light and controlled temperature of the enclosed environment. The at least one culture pipe may be completely transparent or transparent to a degree ranging from 0-100%. In some embodiments, the at least one culture pipe may be comprised of a transparent material suitable for a pipe containing a freshwater or marine aqueous culture medium such as, but not limited to, glass or plastic. The thickness of the pipe material may be any suitable thickness which allows the transmission of light to the interior of the pipe without significant degradation or refraction of the light. The diameter of the at least one culture pipe may be determined based on a desired light path through the pipe, the ability for light to penetrate the culture of microorganisms, the volume of the aqueous culture, or the desired flow rate for the aqueous culture. The length of the at least one culture pipe may be determined based on the desired residence time within the continuous culture profile optimization system, and particularly the residence time within the segment of the system comprising the housing for exposure to the controlled exposure to light and controlled temperature.

To aid the system in continuous optimization of the microorganism culture profile, the flow rate of the aqueous culture through the at least one culture pipe maybe adjusted to achieve a desired residence time. The flow rate may be controlled by an automated computer controller (e.g., programmable logic controller) utilizing a pump, a valve, or gravity. Controlling the residence time of the culture of microorganisms within the system and particularly within the controlled environment of the interior volume of the housing may provide for the desired application of heating, cooling, light exposure, and/or light deprivation and other culture processing which contribute to the continuous optimization of the culture profile. In some embodiments, the flow rate of the culture may be chosen to run the entire culture volume or a portion of the culture volume through the controlled environment apparatus in a desired time frame (e.g., 100% of the culture per day, 50% of the culture every 6 hours). In some embodiments, the cross-section of the at least one culture pipe may be circular, elliptical, square, rectangular, or polygonal. In some embodiments, the length of the at least one culture pipe may extend beyond the length of the housing and through an opening in at least one end or side wall.

The degree of turbulence and mixing within the at least one culture pipe may also be controlled by the flow rate. In some embodiments, the flow of the aqueous culture within the at least one culture pipe may be highly turbulent to allow constant mixing of the microorganisms in the culture. In some embodiments, the flow of the aqueous culture may be of a low turbulence to lower the degree of mixing in the at least one culture pipe. In some embodiments, the interior surface of the at least one culture pipe may comprise baffles to induce a turbulent flow of the culture within the culture pipe. Controlling the flow rate into the culture pipe may also provide a benefit of reducing biofouling by continually flowing the culture through the at least one culture pipe at a velocity and turbulence which reduces the opportunities for components of the culture to settle and attach to the interior surfaces of the at least one culture pipe. Additionally, having multiple culture pipes allows for the option to rotate the culture pipe or pipes which actively contain the aqueous culture of microorganisms while one or more pipes may be empty for cleaning, therefor maximizing the effectiveness of the application of light to the culture and reducing down time.

Through the separation of the aqueous culture of microorganisms and light devices, as opposed to submerging lights in the aqueous culture of microorganisms, the at least one lighting device does not necessitate a mechanism or method to clean the outside of the lighting device to maintain light transmissibility. In an apparatus where lights are submerged in an aqueous culture of microorganisms, biofouling on the surface of the lights may reduce the transmission of light and therefore reduces the effectiveness of the light application.

Sensor Modules

The apparatus may also include sensor modules at multiple locations to continuously measure the parameters of the aqueous culture. The data obtained by the sensor modules may be transmitted to an automated computer controller (e.g., programmable logic controller) to continuously optimize the culture profile through the light, temperature, flow rate, and processing device controls.

The sensor modules may comprise sensors to measure parameters of the aqueous culture such as, but not limited to, culture pH, culture nutrient levels, culture gas levels, culture composition, culture health, contamination levels, culture temperature, flow rate, culture density, ambient environmental temperature, and ambient environmental light. A first sensor module may be disposed at a first location where the aqueous culture exits the culturing vessel and enters the at least one culture pipe, but before introduction into the controlled environment within the housing or the at least one culture processing device. A second sensor module may be disposed at a second location where the culture has exited the controlled environment of the housing and at least one culture processing device but before re-entry into the culturing vessel, or in the alternative exits the system and enters a path for further processing of the culture outside of the continuous culture optimization system, such as dewatering or extraction. In some embodiments, a sensor module may be disposed at a location within the controlled environment of the housing, or other additional locations in the system.

The measurements taken by the sensors are transmitted to an automated computer controller (e.g., programmable logic controller). In some embodiments, the automated computer controller may continuously adjust the parameters such as, but not limited to: flow rate, temperature of the interior volume of the housing, light application within the interior volume of the housing, culture mixing, nutrient addition to the culture, gas exchange with the culture, contamination control, removal of biomass, and removal of water, based on the transmitted sensor data to continuously maintain the culture at an optimized parameter profile. In some embodiments, the automated computer controller may continuously adjust the parameters based on a program with a predetermined schedule to maintain an optimal culture profile. In some embodiments, the application of light may vary with the sensed ambient environment light conditions such as, but no limited to, daytime, night time, clear skies, and cloudy skies. In some embodiments, the conditions within the housing and use of the at least one culture processing device may be continuously adjusted to achieve a desired outcome such as, but not limited to, maximizing culture biomass growth, enhancing the production of a targeted product (e.g. lipids, pigments, phytohormones, proteins), repairing damage to the organisms from over exposure to a particular light spectrum and/or temperature of the outdoor environment, cooling the culture, heating the culture, mitigating culture biomass loss due to respiration, preparing the culture for a further processing step (e.g., providing a finishing step targeted at increasing a cellular product before extraction processing), changing the composition of the culture, and killing select microorganisms within the culture.

Such automated computer controller (e.g., programmable logic controller) and sensor module systems are known by those skilled in the art. In some embodiments, automated computer controller and sensor module systems may control various components of the continuous optimization system via computer, computer processing system with a memory, data logger, programmable logic control, data acquisition unit, any other type of real time monitoring and control system with a memory, or any combination thereof. In some embodiments, the automated computer controller and sensor module systems may be configured to be accessed remotely by a networked computer or a computer processing device with a properly configured application, such as but not limited to, a smartphone with an application configured to access a sensor and control system computer through a data network. In some embodiments, remote access to the sensor and control system allows a user to input or change definitions and instructions for the automated computer controller and sensor module systems and view data produced by the automated computer controller and sensor module systems. In some embodiments, the data logging system comprises a National Instruments, Campbell Scientific, Allen-Bradley product, or combinations thereof.

Such sensors for the sensor modules are also known in the art. In some embodiments, the sensors disclosed herein may comprise: temperature, carbon dioxide, ozone, redox potential, dissolved oxygen, light (watts/meter$^2$), light ($\mu$mols/meter$^2$ day), light wavelength (nm), relative humidity, air speed, pH, chlorophyll A, phycobilins, phycocyanins, turbidity, color, density, salt content/concentration, optical density, electrical conductivity sensors, and combinations thereof. In some embodiments, the sensors may comprise Campbell Scientific, Honeywell, YSI, National Instruments, Heliae designed sensors, Hanna Instruments products, and combinations thereof. Additional sensors commercially available for aquacultures comprise ammonia/ammonium, biochemical oxygen demand (BOD), chloride, nitrate, rhodamine, total dissolved solids (TDS), phosphate, and various trace metal (i.e., Pb, Hg, Bi, As, Sb, Sn, Cd, Ag, Cu, Mo) sensors.

In some embodiments, sensors disclosed herein may comprise a Red-Green-Blue (RGB) sensor to monitor the color and density of the microorganisms contained in the aqueous culture. In some embodiments, the RGB sensors may comprise an OPTEK Technology product. The color and density feedback provided by the RGB sensor may be analyzed by the automated computer controller (e.g., programmable logic controller) to provide information regarding the health of the microorganisms in the aqueous culture, level of contamination in the aqueous culture, the composition of the aqueous culture, and other critical conditions. The RGB sensor may additionally comprise a translation circuit to match the sensor output to a format readable by the automated computer controller.

In some embodiments, the sensor modules may comprise a fluorescence scan. In these embodiments, the sensor module may perform a fluorescence scan of the aqueous culture before the aqueous culture enters and/or after the culture exits the controlled environment of the housing or culture processing devices to determine the composition and profile of the culture in real time. By scanning the aqueous culture with fluorescent lighting, different organisms (e.g., microalgae species, bacteria, rotifers) in the culture may fluoresce differently (i.e., fluoresce at different spectrums). The fluorescing of the different organisms may be detected by sensors, which transmit the data to the automated computer controller. The automated computer controller may utilize the fluorescence data to continuously adjust the parameters such as, but not limited to: flow rate, temperature of the interior volume of the housing, light application within the interior volume of the housing, culture mixing, nutrient addition to the culture, gas exchange with the culture, contamination control, removal of biomass, and removal of water based on the fluorescence data in real time to achieve a desire outcome such as, but not limited to maintaining an optimal culture profile or killing select contaminating organisms in the culture.

Pipe Configuration

Any number of lighting devices and culture pipes may be used which fit within the interior volume of the housing and the system. In some embodiments, a single lighting device may be disposed centrally within the interior volume of the housing and surrounded by a plurality of culture pipes disposed between the lighting device and housing. The plurality of culture pipes may run parallel to and be spaced circumferentially around the lighting device for even light distribution to the culture. In further embodiments, the housing may contain multiple clusters of pipes comprising a plurality of culture pipes spaced and surrounding a lighting device. In some embodiments, the housing may comprise multiple lighting devices distributed to evenly light the at least one culture pipe. In some embodiments, the at least one lighting device may be disposed in a position not centered within the housing. In some embodiments, the system may comprise at least three culture pipes. In some embodiments, the diameters of the at least one lighting device and the at least one culture pipe may be the same. In some embodiments, the diameters of the at least one lighting device and the at least one culture pipe may be different.

Method

The system described above may be used in a method for continuously optimizing the profile of a microorganism culture, comprising: growing a culture of microorganisms in an aqueous medium in a culturing vessel exposed to an ambient environment; removing at least a portion of the aqueous culture from the culturing vessel and transferring the removed aqueous culture to at least one culture pipe; measuring at least one parameter of the removed aqueous culture and ambient environment with at least one sensor before the aqueous culture enters a housing or a culture processing device; flowing the removed aqueous culture through the at least one culture pipe from a first end of the at least one culture pipe to a second end of the at least one culture pipe, wherein the at least one culture pipe is at least partially disposed within an interior volume of the housing; applying light to the removed aqueous culture flowing through a transparent length of the at least one culture pipe between the first end and the second end disposed within the interior volume of the housing with at least one lighting device disposed within an interior volume of the housing; controlling the temperature of the interior volume within the housing; and measuring at least one parameter of the removed aqueous culture with sensors at a point before the aqueous culture is returned to the culturing vessel. The method may further comprise processing the removed culture in a culture processing device in at least one from the group consisting of: a mixing process, nutrient addition, gas exchange, pH adjustment, contamination control, removal of biomass, and water removal.

In some embodiments, the steps of measuring the parameters of the removed culture may further comprise fluorescing the removed culture to detect the composition of the culture. In some embodiments, the step of applying light may further comprise light of at least one limited wavelength range selected from the group consisting of: violet (about 380-450 nm), blue (about 450-495 nm), green (about 495-570 nm), yellow (about 570-590 nm), orange (about 590-620 nm), red (about 620-750 nm), far red (about 700-800 nm), infrared (IR) (about 1,000-20,000 nm) and ultraviolet (UV) (about 10-400 nm). In some embodiments, the step of controlling the temperature of the interior volume within the housing may comprise at least one selected from the group consisting of: circulating a cooling fluid in the interior volume, circulating a heating fluid in the interior volume, circulating air in the interior volume, and operating a heat exchanger.

In some embodiments, the parameters measured by the sensors may comprise at least one selected from the group consisting of: culture pH, culture nutrient levels, culture gas levels, culture composition, culture health, contamination levels, culture temperature, flow rate, culture density, ambient environmental temperature, and ambient environmental light. In some embodiments, the method further comprises adjusting at least one from the group consisting of: flow rate, temperature of the interior volume of the housing, light application within the interior volume of the housing, culture mixing, nutrient addition to the culture, gas exchange with the culture, contamination control, removal of biomass and removal of water, with an automated computer controller receiving the culture parameters measured by the sensors.

In one non-limiting exemplary embodiment, the at least one culture pipe may receive a volume of an aqueous culture comprising microorganisms at a first end of the at least one culture pipe from a culturing vessel. The parameters of the aqueous culture may be measured by a first sensor module and transmitted to an automated computer controller. In some embodiments, the first end of the culture pipe may branch into multiple culture pipes within the housing. The aqueous culture may flow through the at least one culture pipe to a second end of the culture pipe, including through the length of the at least one culture pipe contained within the housing. At the second end of the culture pipe, the aqueous culture exits the housing. The aqueous culture may be processed by at least one culture processing device before entering the housing, after exiting the housing, or both. The parameters of the aqueous culture may be measured by a second sensor module and transmitted to the automated computer controller before being re-introduced to the culturing vessel. In some embodiments, multiple culture pipes within the housing may merge into a single culture pipe at the second end. In other embodiments, multiple culture pipes may receive a volume of the aqueous culture from the growth vessel and flow the culture through the controlled environment apparatus without branching. As the aqueous culture passes through the portion of the at least one culture pipe in the interior volume of the housing, the aqueous culture may be exposed to a controlled environment.

In some embodiments, the environment within the interior volume of the housing comprises heated or cooled fluid, gas, liquid, or air. In some embodiments, the environment within the housing may be dark with no light. In some embodiments, the at least one lighting device may emit light of a desired wavelength and intensity into the interior of the housing continuously or intermittently. The emitted light may comprise at least one type of light selected from the group consisting of: violet (about 380-450 nm), blue (about 450-495 nm), green (about 495-570 nm), yellow (about 570-590 nm), orange (about 590-620 nm), red (about 620-750 nm), far red (about 700-800 nm) light, infrared (IR) (about 1,000-20,000 nm), and ultraviolet (UV) (about 10-400 nm). The emitted light of the desired wavelength may penetrate the transparent material of the at least one culture pipe and be received by the microorganisms. The data transmitted from the sensor modules to the automated computed controller may be used to continuously adjust the light application, temperature control, and culture processing devices to maintain an optimal culture profile.

Example Embodiments

Aspects of the system for continuously optimizing a culture profile are further described in the non-limiting exemplary embodiments shown in FIGS. 1-5. Particularly, FIGS. 1-4 show a controlled environment apparatus comprises: a housing comprising an interior volume; at least one lighting device comprising an artificial light source disposed within the interior volume of the housing; at least one culture pipe configured to hold an aqueous culture medium comprising microorganisms, wherein the at least one culture pipe comprises a transparent material and is disposed at least partially within the interior volume of the housing to receive light from the at least one lighting device; and a temperature control device configured to control the temperature of the interior volume within the housing.

Figure 1:
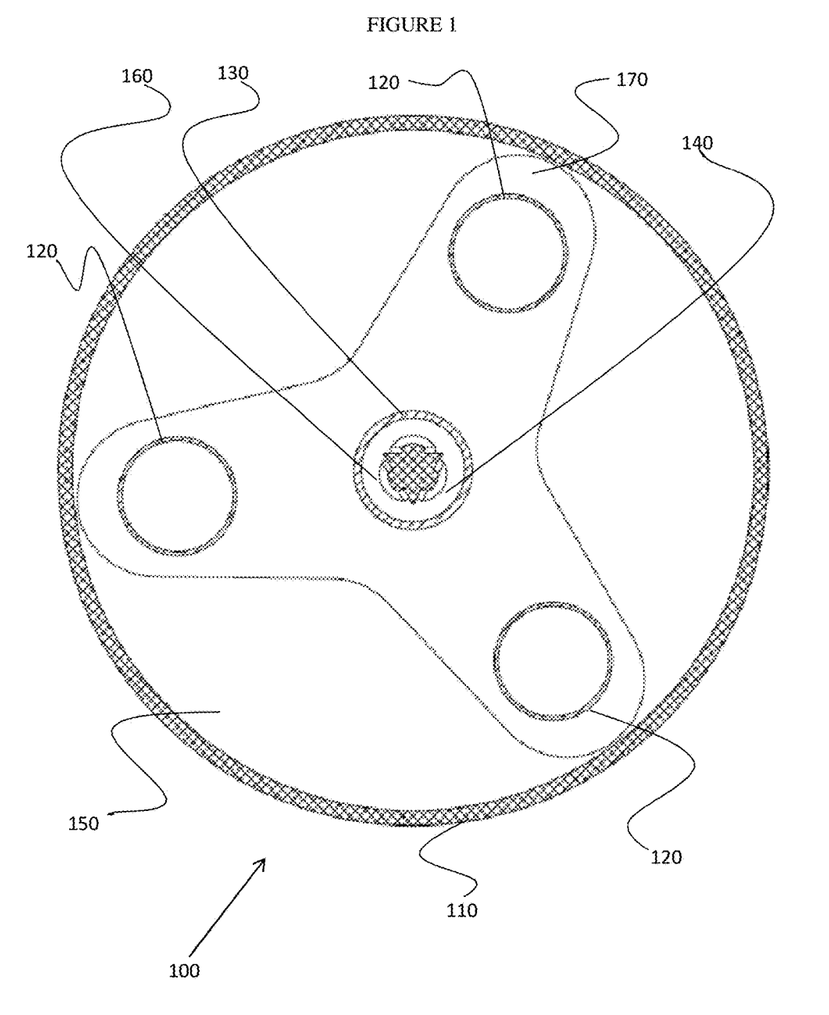
FIG. 1 shows a cross-sectional view of a first exemplary embodiment of the invention.
Figure 2:
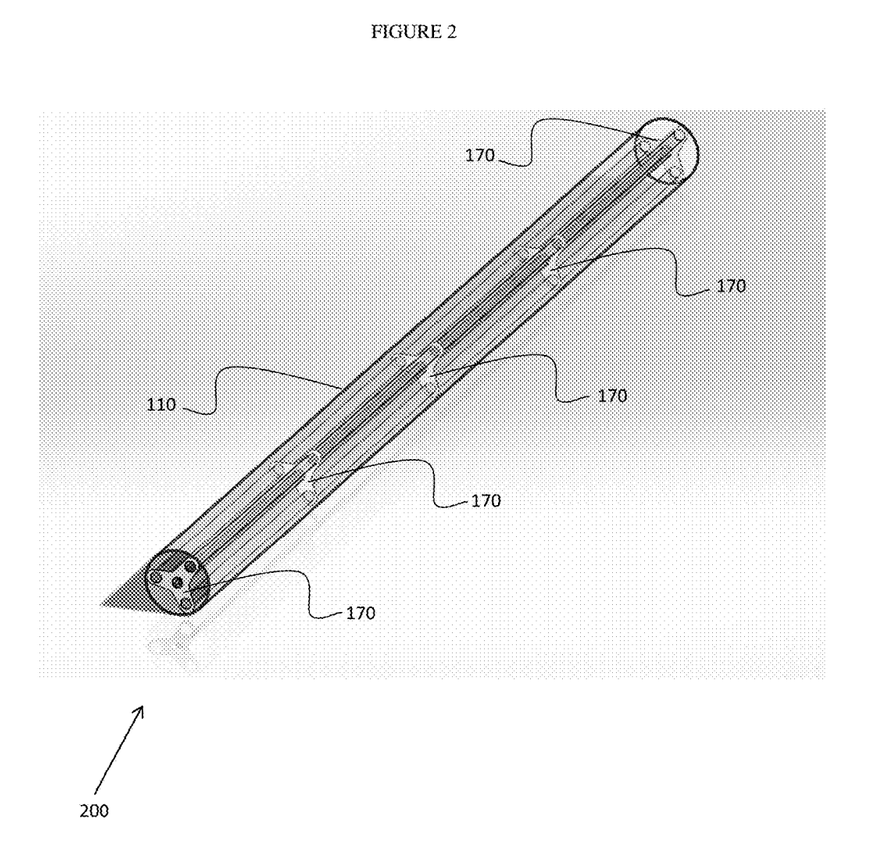
FIG. 2 shows an isometric view of the first exemplary embodiment of the invention illustrating the spaced bracket members.

A first exemplary embodiment is illustrated in FIGS. 1 and 2. Referring to FIG. 1, a cross-sectional view of the controlled environment apparatus 100 is shown. The housing 110 encloses a lighting pipe 130 disposed within the circular housing 110. The interior volume 150 within the housing is a controlled environment that may be heated or cooled. Within the lighting pipe 130 is a multisided artificial light source 140 comprising panels of LEDs facing each culture pipe 120. The space 160 within the lighting pipe may be a controlled environment that may be heated or cooled. The culture pipes 120 are disposed between the lighting pipe 130 and the housing 110, and are spaced in a circumferential manner around the lighting pipe 130 for even light distribution to the culture pipes 120. The culture pipes 120 and lighting pipe 130 are held in position within the housing 110 by the bracket 170. Referring to FIG. 2, a view of the apparatus 200 illustrates one non-limiting spacing arrangement of the brackets 170 within the housing 110 in which the lighting pipe and culture pipes run parallel to each other and the longitudinal axis of the housing 110.

Figure 3:
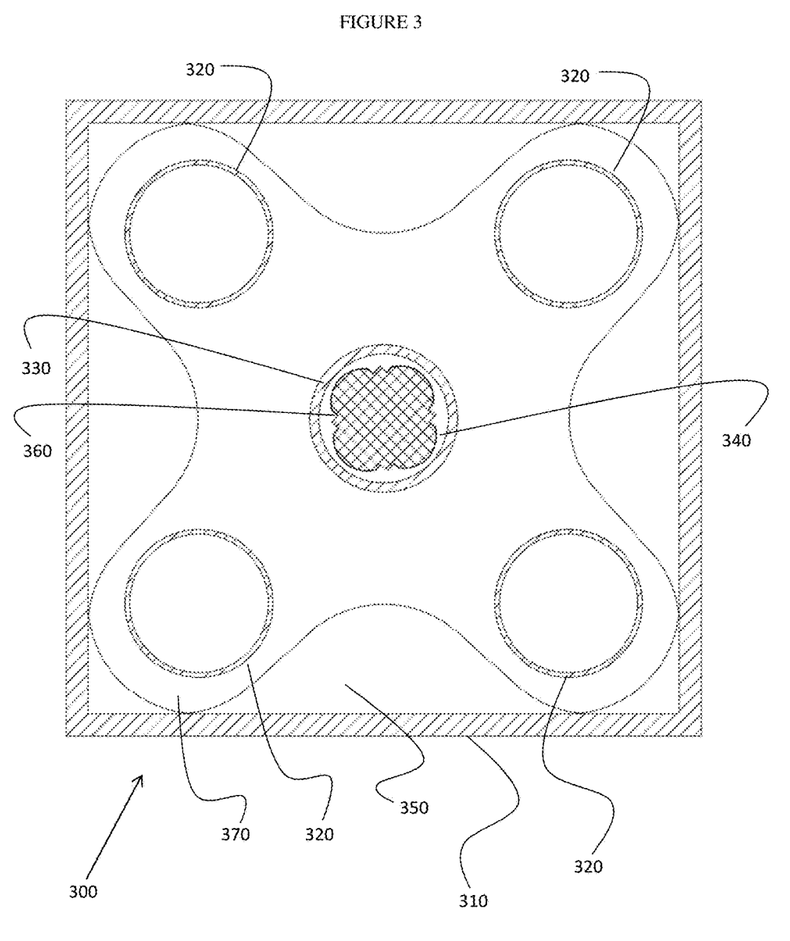
FIG. 3 shows a cross-sectional view of a second exemplary embodiment of the invention.

Referring to FIG. 3, a cross-sectional view of a second exemplary embodiment of the controlled environment apparatus 300 is shown. The housing 310 encloses a lighting pipe 330 disposed within the rectangular housing 310. The interior volume 350 within the housing is a controlled environment that may be heated or cooled. Within the lighting pipe 330 is a multisided, artificial light source 340 comprising panels of LEDs facing each culture pipe 320. The space 360 within the lighting pipe may be a controlled environment that may be heated or cooled. The culture pipes 320 are disposed between the lighting pipe 330 and the housing 310, and are spaced in a circumferential manner around the lighting pipe 330 for even light distribution to the culture pipes 320. The culture pipes 320 and lighting pipe 330 are held in position within the housing 310 by the bracket 370.

Figure 4:
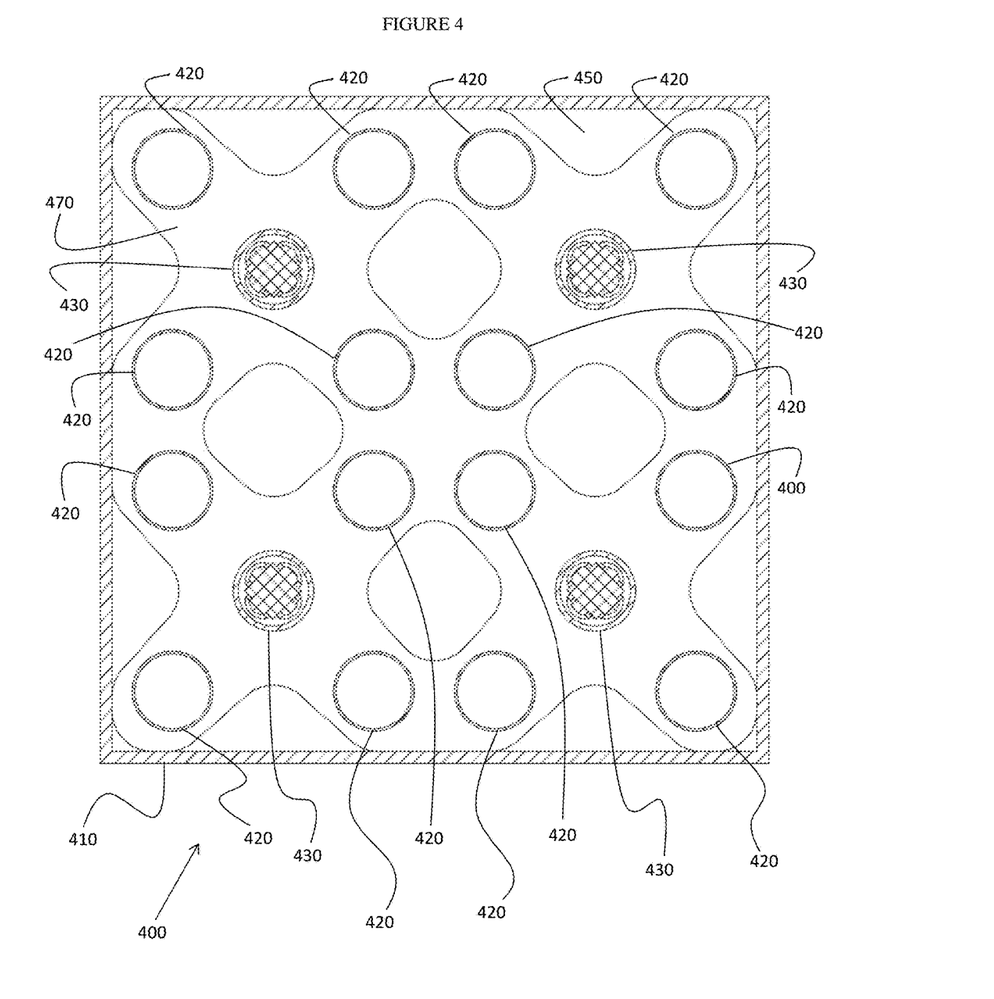
FIG. 4 shows a cross-sectional view of a third exemplary embodiment of the invention.

Referring to FIG. 4, a cross-sectional view of a third embodiment of the controlled environment apparatus 400 illustrates an embodiment with an array of lighting pipe 430 and culture pipe 420 clusters disposed with in the housing 410. Within the lighting pipes 430 are multisided artificial light sources comprising panels of LEDs facing each culture pipe 420. Within each cluster, the culture pipes 420 are disposed between the lighting pipe 430 and the housing 410, and are spaced in a circumferential manner around the lighting pipe 430 for even light distribution to the culture pipes 420. The culture pipes 420 and lighting pipes 430 are held in position within the housing 410 by the bracket 470. The interior space 450 within the housing is a controlled environment that may be heated or cooled.

Figure 5:
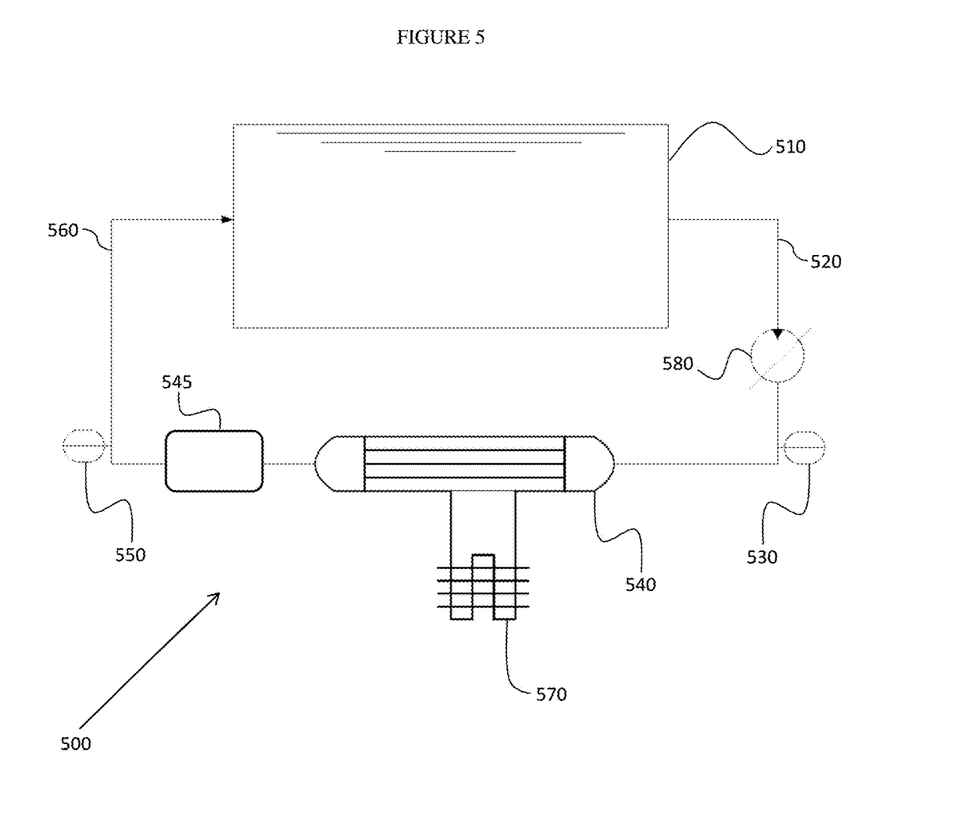
FIG. 5 shows a mechanical diagram of an exemplary system embodiment.

Referring to FIG. 5, a mechanical diagram of an exemplary embodiment of a system 500 for continuously optimizing a culture profile is shown. A culturing vessel 510 (e.g., pond, photobioreactor, tank, trough, raceway pond) contains an aqueous culture of microorganisms. At least a portion of the aqueous culture exits the culturing vessel 510 at a first end and enters piping 520 which carries the culture from the culturing vessel 510 to a first end of the controlled environment apparatus 540. The flow of the aqueous culture may split into multiple culture pipes upon exiting the culturing vessel 510 or upon entering the controlled environment apparatus 540. A first sensor module 530 is located in line with piping 520 to measure parameters of the aqueous culture and the ambient environment before the aqueous culture enters the first end of the controlled environment apparatus 540. A temperature control device 570 may heat or cool the interior environment of the controlled environment apparatus 540, which also comprises at least one lighting device. The culture exits the controlled environment apparatus 540 at a second end and flows through at least one culture processing device 545 and piping 560 to a second end of the culturing vessel 510 where the culture is re-introduced into the culturing vessel 510. The flow of the aqueous culture may condense from multiple culture pipes to a single pipe upon exiting the controlled environment apparatus 540 and re-entering the growth vessel 510. A second sensor module 550 is located in line with piping 560 to measure parameters of the aqueous culture and the environment as the culture exits the second end of the controlled environment apparatus 540 and at least one culturing processing device 545.

The diagram shows at least one culture processing device 545 located in line between the controlled environment apparatus 540 and sensor module 550, but the at least one culture processing device 545 may also be located between the sensor module 530 and the controlled environment apparatus 540 or in both locations. A pump 580 controls the flow of the aqueous culture through the piping 520, 560 and controlled environment apparatus 540. The first sensor module 530, second sensor module 550, pump 580, temperature control device 570, at least one culture processing device 545 and controlled environment apparatus 540 may communicate with an automated computer controller (not shown) for continuous adjustment of culture parameters to maintain an optimal culture profile, and receive power from an external power source (not shown).

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A system for continuously optimizing the profile of a culture of microorganisms, comprising
   a. An open raceway pond configured to grow a culture of microorganisms in an aqueous culture medium;
   b. A controlled environment apparatus, wherein the system is configured to circulate at least a portion of the culture of microorganism through the open raceway pond and controlled environmental apparatus, the controlled environment apparatus comprising:
      i. A housing comprising a closed interior volume;
      ii. At least one artificial lighting device disposed within the interior volume of the housing;
      iii. A plurality of culture pipes defining a plurality of separate flow paths, each culture pipe with a first end and second end in fluid communication with the open raceway pond, configured to hold an aqueous culture medium comprising microorganisms, and wherein each culture pipe comprises a transparent portion disposed at least partially within the interior volume of the housing;
      iv. A temperature control device configured to control the temperature of the interior volume within the housing;
      v. At least one bracket spaced along a longitudinal axis of the housing between the first ends and second ends of the plurality of culture pipes, and configured to support the plurality of culture pipes and the at least one artificial lighting device;
   c. A first sensor module disposed in a first location to measure at least one parameter of the culture of microorganisms in the aqueous culture medium at the first end of at least one of the plurality of culture pipes; and
   d. At least one contamination control device in fluid communication with the controlled environment apparatus and the open raceway pond, wherein the contamination control device is disposed after the controlled environment apparatus in a culture circulation path.

2. The system of claim 1, further comprising a second sensor module disposed in a second location to measure at least one parameter of the culture of microorganisms in the aqueous culture medium at the second end of at least one of the plurality of culture pipes.

3. The system of claim 2, wherein at least one of the first sensor module and the second sensor module comprise at least one sensor selected from the group consisting of: temperature, carbon dioxide, ozone, redox potential, dissolved oxygen, light (watts/meter$^2$), light (mols/meter$^2$ day), light wavelength (nm), relative humidity, air speed, pH, chlorophyll A, phycobilins, phycocyanins, turbidity, color, density, salt content/concentration, optical density, electrical conductivity sensors, and fluorescence sensors.

4. The system of claim 3, wherein the at least one of the first sensor module and the second sensor module comprise a fluorescence scan.

5. The system of claim 1, further comprising a pump to circulate the aqueous culture medium through the system in a circulation path.

6. The system of claim 1, further comprising an automated computer controller, wherein the automated computer controller is configured to continuously receive data from the first and second sensor modules and adjust at least one from the group consisting of: a flow rate of the aqueous culture medium, temperature of the interior space of the housing, light application within the interior space of the housing, mixing of the aqueous culture medium, and contamination control of the aqueous culture medium.

7. The system of claim 1, wherein the at least one artificial lighting device comprises at least one selected from the group consisting of light emitting diodes (LEDs), micro-LEDs, and light bulbs.

8. The system of claim 1, wherein the at least one artificial lighting device emits light in at least one limited wavelength range selected from the group consisting of: violet (about 380-450 nm), blue (about 450-495 nm), green (about 495-570 nm), yellow (about 570-590 nm), orange (about 590-620 nm), red (about 620-750 nm), far red (about 700-800 nm), infrared (IR) (about 1,000-20,000 nm) and ultraviolet (UV) (about 10-400 nm).

9. The system of claim 1, wherein the at least one artificial lighting device comprises at least one selected from the group consisting of: a continuous light source along the length of the housing and discretely spaced light sources within the housing.

10. The system of claim 1, wherein the temperature control device comprises at least one selected from the group consisting of: an HVAC unit, a heat exchanger, heating coils, cooling coils, and a fan.

11. The system of claim 1, wherein the cross-section of the at least one culture pipe is circular, elliptical, square, rectangle, or polygonal.

12. The system of claim 1, wherein the plurality of culture pipes further comprise baffles disposed on an interior surface of at least one culture pipe.

13. The system of claim 1, wherein the housing blocks the transmission of at least some light from passing through to the plurality of culture pipes.

14. The system of claim 1, wherein the contamination control device comprises at least one selected from the group consisting of: a protein skimmer and an ultraviolet (UV) sterilizer.

15. The system of claim 1, wherein the bracket is transparent to a degree which allows the transmission of at least some light.

16. The system of claim 1, wherein the at least one lighting device is disposed in a position not centered in the housing.

17. A system for continuously optimizing the profile of a culture of microorganisms, comprising:
   a. An open raceway pond configured to grow a culture of microorganisms in an aqueous culture medium;
   b. A controlled environment apparatus, wherein the system is configured to circulate at least a portion of the culture of microorganism through the open raceway pond and controlled environmental apparatus, the controlled environment apparatus comprising:
      i. A housing comprising a closed interior volume;
      ii. At least one artificial lighting device disposed within the interior volume of the housing;
      iii. A plurality of culture pipes defining a plurality of separate flow paths, each culture pipe with a first end and second end in fluid communication with the open raceway pond, configured to hold an aqueous culture medium comprising microorganisms, and wherein each culture pipe comprises a transparent portion disposed at least partially within the interior volume of the housing;
      iv. A temperature control device configured to control the temperature of the interior volume within the housing;
      v. At least one bracket spaced along a longitudinal axis of the housing between the first ends and second ends of the plurality of culture pipes, and configured to support the plurality of culture pipes and the at least one artificial lighting device;
c. A first sensor module disposed in a first location to measure at least one parameter of the culture of microorganisms in the aqueous culture medium at the first end of at least one of the plurality of culture pipes; and
d. At least one contamination control device in fluid communication with the controlled environment apparatus and the open raceway pond, wherein the contamination control device comprises at least one selected from the group consisting of: a protein skimmer and an ultraviolet (UV) sterilizer.

* * * * *